United States Patent
Goebel et al.

(12) 
(10) Patent No.: US 6,428,514 B1
(45) Date of Patent: Aug. 6, 2002

(54) DEVICE FOR ADMINISTERING LIQUIDS TO A PATIENT

(75) Inventors: Udo Goebel, Melsungen-Kirchhof; Manfred Friederichs, Melsungen; Volker Harms, Kassel; Manfred Heitmann, Haan; Tabea Hinkel, Melsungen; Karl-Heinz Koch, Melsungen; Hans-Joachim Otto, Melsungen; Klaus Siemon, Koerle; Martin Sippel, Melsungen, all of (DE)

(73) Assignee: B. Braun Melsungen AG, Melsungen (DE)

( * ) Notice: Subject to any disclaimer, the term of this patent is extended or adjusted under 35 U.S.C. 154(b) by 0 days.

(21) Appl. No.: 09/554,394

(22) Filed: Jul. 5, 2000

(30) Foreign Application Priority Data

Nov. 14, 1997 (DE) .......................................... 297 20 182

(51) Int. Cl.⁷ ............................................... A61M 5/32
(52) U.S. Cl. ......................... 604/174; 604/180; 604/177
(58) Field of Search ................................ 604/174, 180, 604/177, 179, 178; 128/DIG. 26

(56) References Cited

U.S. PATENT DOCUMENTS

| 5,456,671 | A |   | 10/1995 | Bierman |            |
|-----------|---|---|---------|---------|------------|
| 5,496,283 | A | * | 3/1996  | Alexander | 604/180  |
| 5,681,290 | A | * | 10/1997 | Alexander | 604/180  |
| 5,690,617 | A | * | 11/1997 | Wright    | 604/179  |
| 5,800,402 | A | * | 9/1998  | Bierman   | 604/180  |
| 5,810,781 | A | * | 9/1998  | Bierman   | 604/174  |
| 5,944,696 | A | * | 8/1999  | Bayless et al. | 604/174 |
| 5,947,931 | A | * | 9/1999  | Bierman   | 604/180  |
| 6,132,398 | A | * | 10/2000 | Bierman   | 604/174  |
| 6,213,979 | B1 | * | 4/2001 | Bierman   | 604/174  |
| 6,224,571 | B1 | * | 5/2001 | Bierman   | 604/174  |
| 6,290,676 | B1 | * | 9/2001 | Bierman   | 604/174  |
| 6,332,874 | B1 | * | 12/2001 | Eliasen et al. | 604/174 |

* cited by examiner

*Primary Examiner*—Teresa Walberg
*Assistant Examiner*—Fadi H. Dahbour
(74) *Attorney, Agent, or Firm*—Diller, Ramik & Wight

(57) ABSTRACT device for administering liquids comprises an administering part (10) and an adhesive plaster (11). The administering part (10) is connected with a cannula stud (30) and an administering line (14) and carries a liquid. For fastening the administering part (10) to the surface of a patient's skin or the surface of an object the adhesive plaster (11) is stuck on the surface. The adhesive plaster (11) is provided with a plug-in pin (38) which is adapted to be inserted into an insertion opening (43) of the filter (10). By placing the filter (10) onto the plug-in pin (38) the administering part (10) is detachably connected with the adhesive plaster (11). If the administering part (10) is a filter with transparent housing the filter membrane is well visible since the latter is not covered by adhesive strips when the filter is fastened to the patient's body.

9 Claims, 3 Drawing Sheets

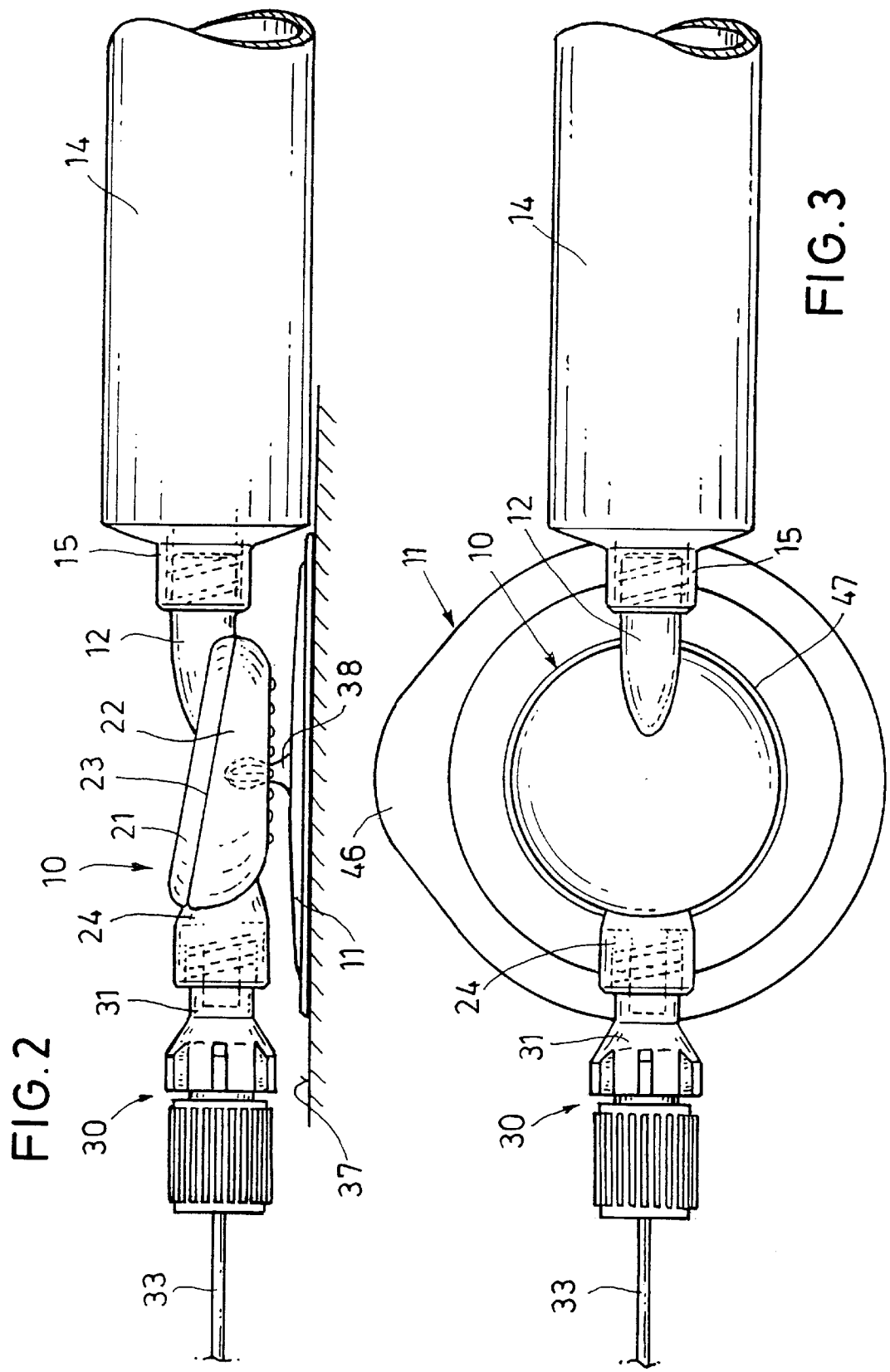

FIG.4
FIG.5
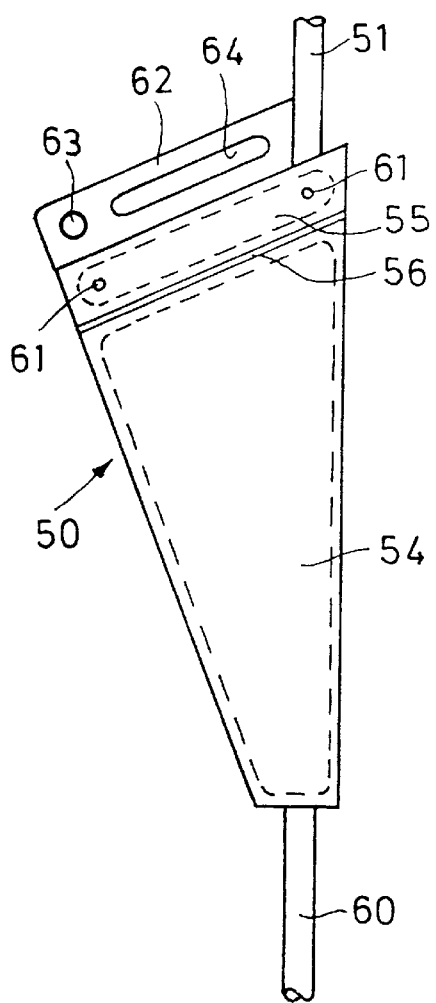
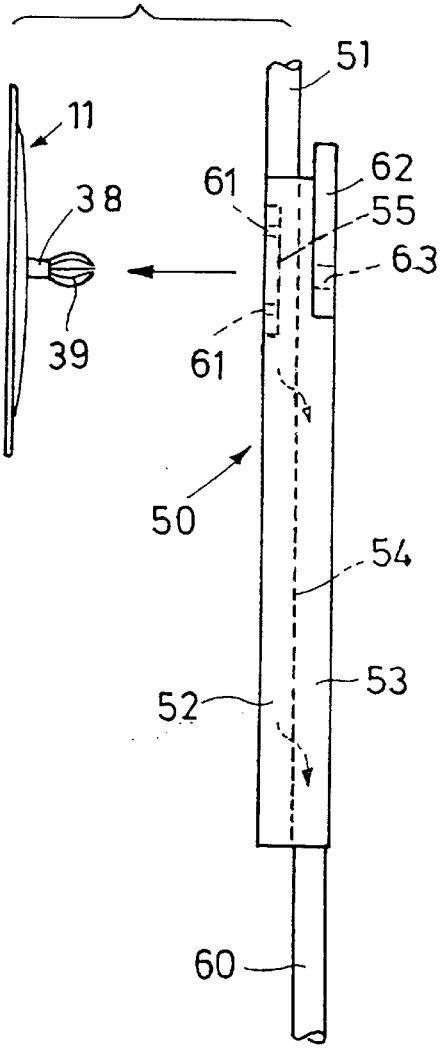

DEVICE FOR ADMINISTERING LIQUIDS TO A PATIENT

BACKGROUND OF THE INVENTION

The invention relates to a device for administering liquids to a patient, the device comprising an adminstering part and a fastening part. The administering part, through which the liquid can flow, is, for example, a cannula stud, a catheter stud or a filter. The adminstering part is fastened by the fastening part, for example, to the skin of the patient, his clothes, a patient's bed, an infusion stand or other objects.

Normally administering parts are fastened to a patient's body by means of adhesive plaster with the adhesive plaster strips extending over the administering part. Particularly in the case of filters such indiscriminate glueing-over results in the filter not being capable of being inspected any more. To check whether the filter is fouled it is necessary to remove the adhesive plaster strips from the skin. In particular when different medicines are administered to the patient via one and the same access it is important to frequently check the filter since different medicines may interreact and crystallize. This may result in the filter becoming blocked. Filters glued over with adhesive plaster do not allow the filter to be continuously observed so that they are concealed from the physician's control to a large extent. Further, in the case of infusions filters are used for filtering bacteria and particles over a long period and must therefore be replaced at certain intervals.

Short catheters which are fastened near the puncture site on the surface of the skin partly comprise wing-shaped studs made of plastic material. To fasten the short catheters adhesive plaster strips are stuck over the wing-shaped studs.

This type of fastening filters or catheters to a patient's skin limits the freedom of movement of the patient and may lead to injuries when the patient moves.

From U.S. Pat. No. 5,456,671 fastening of a catheter with an adhesive plaster to a patient's skin is known. For this purpose the adhesive plaster comprises a first coupling part having a longitudinal slot into which the catheter can be inserted. Although the catheter can be detached from the coupling part without the adhesive plaster being removed from the patient's skin the catheter is retained in the coupling part so that the freedom of movement of the patient continues to be considerably limited.

SUMMARY OF THE INVENTION

It is the object of the invention to create a device for administering liquids to a patient, which is adapted to be fastened to the patient's body or any other carrier in a simple way, which can be easily and rapidly detached and limits the patient's freedom of movement to the smallest extent possible.

The administering part is fixed by means of a fastening part executed as adhesive plaster with the fastening part comprising a first coupling part releasably engaging with a second coupling part provided on the administering part. According to the invention one of the two coupling parts is configured as plug-in pin and the other coupling part as round insertion opening. Owing to the configuration of the coupling parts according to the invention the administering part can be rotated relatively to the adhesive plaster. This increases the patient's freedom of movement and reduces the danger of injuries during movement. Rotatability of the administering part prevents, for example, a needle inserted into a vein from piercing through the vein when the patient moves.

The adhesive plaster is stuck on the surface of the skin or the surface of an object. The administering part can be fixed to and detached from the fastening part in a simple way by means of the coupling parts. Thus it is not necessary that adhesive plaster strips extend over the administering part and cover it when the administering part is fastened. If the administering part is a filter, said filter can be easily inspected. Since the filter is detachably connected with the fastening part via coupling parts, the filter may be rapidly and easily taken off the fastening part for the purpose of inspecting the bottom side of the filter or exchanging the filter without the fastening part having to be removed from the surface of the patient's skin or the surface of an object.

The coupling parts may be configured such that the administering part is detachably fixed by clamping one of the two administering parts to the other administering part. Alternatively, the coupling parts may be provided with a locking pin or similar such that releasing the connection is possible only be unlocking the coupling parts.

Preferably the two coupling parts are configured as releasable snap elements. At least one of the two snap elements is at least partly elastic and snaps, in assembled condition, the mating coupling part. To release the snap connection the snap elements may be configured such that the elastic part of one snap element must be pushed back by hand before the administering part can be removed from the adhesive plaster. Preferably the snap elements are configured such that the administering part can be detached by being taken off the snap element of the adhesive plaster. For this purpose the elastic part of the snap element may be arcuate such that the elastic part of the snap element is automatically pushed back when the administering part is taken off. When the snap elements are configured in such a way it is not necessary to push back by hand the elastic part of one of the snap elements.

To allow the patient to freely move to a large extent, the plug-in pin comprises an at least partly spherical portion. Such a configuration of the plug-in pin does not only allow the administering part to be rotated about the longitudinal axis of the plug-in pin but it can also be tilted relatively to the longitudinal axis. Thus the connection of the plug-in pin with the insertion opening is a ball-and-socket joint.

To allow the adhesive plaster to be made from very thin flexible material so that it adheres even to uneven surfaces the plug-in pin is preferably provided on the plaster and the insertion opening in the administering part. The insertion opening may be configured as pocket hole or through hole.

Hereunder the invention is explained in detail with reference to preferred embodiments and the drawings in which:

BRIEF DESCRIPTION OF THE DRAWINGS

FIG. 2 shows a schematic side view of the first preferred embodiment;

FIG. 3 shows a schematic top view of the first preferred embodiment;

FIG. 4 shows a schematic top view of a second preferred embodiment; and

FIG. 5 shows a schematic side view of the second preferred embodiment.

DESCRIPTION OF THE PREFERRED EMBODIMENTS

Figure 1:
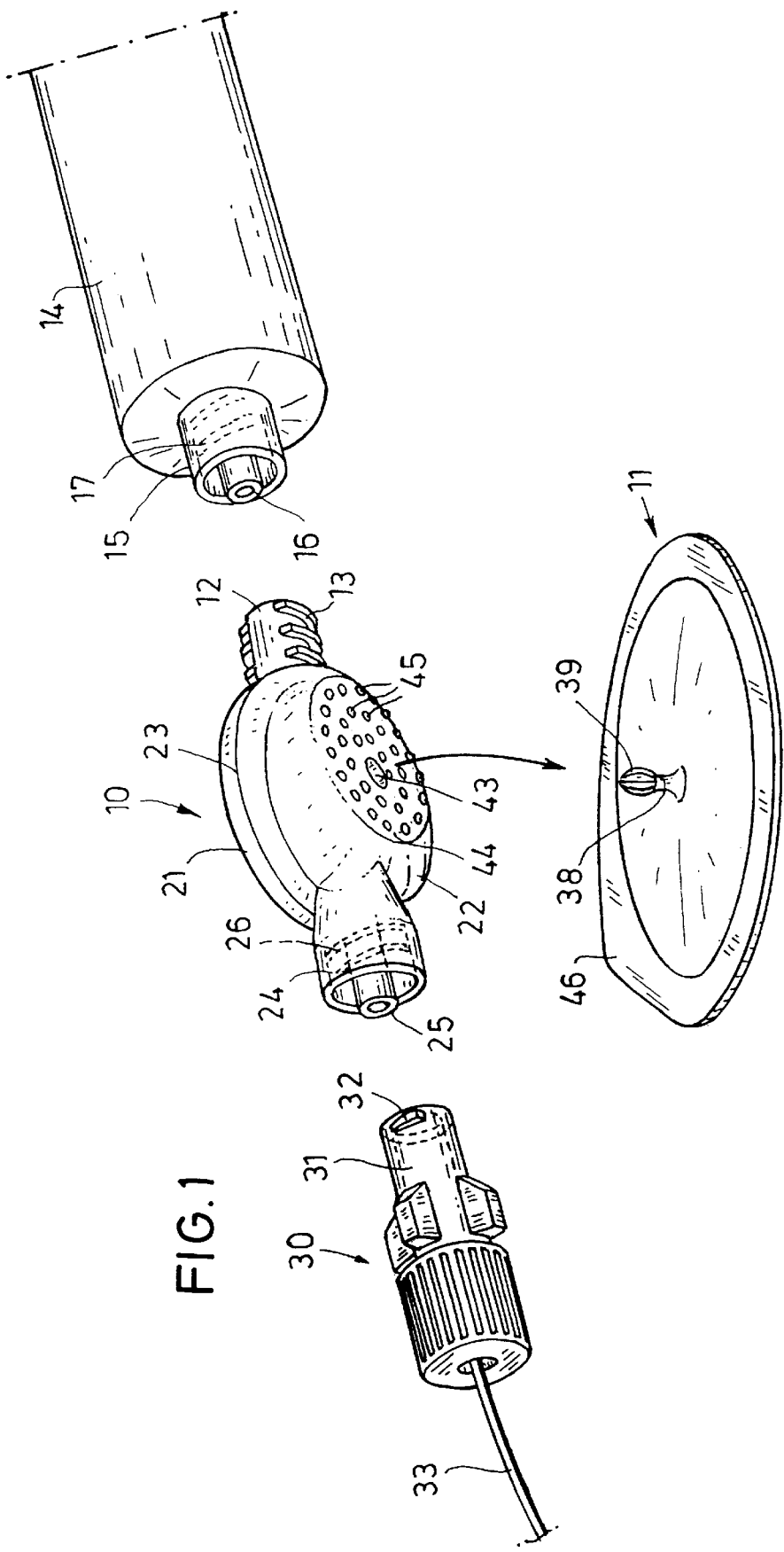
FIG. 1 shows a schematic perspective view of a first preferred embodiment.

The device for administering liquids to a patient as shown in FIGS. 1 to 3 comprises an administering part in the form of a filter 10 for filtering particles or bacteria, and an adhesive plaster 11 with which the filter 10 may releasably engage as will be described below. The filter 10 comprises a cylindrical inlet stud 12 with a male thread 13. A syringe barrel 14 or an administering line connected with a storage tank may be positively connected via a cylindrical stud 15 with the inlet stud 12. Thus instruments for both infusion and injection may be connected to the filter 10 or another administering part. For this purpose the stud 15 comprises a cylindrical connecting piece 16 arranged concentrically to the stud 15. The outer diameter of the connecting piece 16 corresponds to the inner diameter of the inlet stud 12 of the filter 10. To allow the syringe barrel 14 to be positively connected with the filter 10 the stud 15 comprises a female thread 17 which engages with the male thread 13 of the inlet stud 12.

The inlet stud 12 of the filter 10 is connected with an upper filter portion 21 such that the liquid is fed via the syringe barrel 14 into the upper filter portion 21 (FIG. 2). A lower filter portion 22 is connected with the upper filter portion 21 with a filter membrane 23 being arranged on the separating plane of the two filter portions. The liquid is fed from the upper filter portion 21 through the filter membrane to the lower filter portion 22. The lower filter portion 22 comprises a cylindrical outlet stud 24 which has a concentrical connecting piece 25 and a female thread 26 corresponding to the stud 15 of the syringe barrel 14. The outlet stud 24 of the filter 10 is adapted to be connected with a cannula stud 30. For this purpose the cannula stud 30 comprises a cylindrical end 31 whose outer diameter corresponds to the inner diameter of the outlet stud 24 of the filter 10. At the cylindrical end 31 of the cannula stud 30 a projection 32 or a male thread is provided which engages with the male thread 26 of the outlet stud 24 of the filter 10 such that the filter 10 is positively and tightly connected with the cannula stud 30. The cannula stud 30 is connected with a cannula 33 which leads to a patient's body.

The adhesive plaster 11 is provided with an adhesive film on its bottom side such that it can be stuck on the skin 37 of a patient (FIG. 2) or on the surface of an object, e. g. a patient's bed or an incubator. The adhesive plaster 11 made from flexible material comprises a centrally arranged plug-in pin 38 which vertically projects from the surface when the adhesive plaster 11 is stuck on a surface. The plug-in pin 38 is provided with a thickened head and comprises elastic elements 39 on its head, which elastic elements 39 can be compressed from the position shown in FIG. 1 such that the head of the plug-in pin 38 becomes narrower. As soon as pressure force is no longer applied to the elastic elements 39 of the plug-in pin, the elastic elements 39 automatically return into the initial position shown in FIG. 1.

For fastening the filter 10 to the adhesive plaster 11 the filter 10 comprises an insertion opening 43. The insertion opening 43 is executed as a pocket hole expanded to the inside (FIG. 2). Thus the filter 10 can be snapingly fixed by placing the filter 10 onto the plug-in pin 38. Owing to the curved configuration of the elastic elements 39 and the mating shape of the insertion openings 43 the filter 10 can be easily taken off the plug-in pin 38. It is not necessary to release the snap connection by an additional manipulation. Since the insertion opening 43 is round, the filter 10 can be rotated relatively to the plaster 11.

Owing to the round configuration of the insertion opening 43 and the spherical thickened head of the plug-in pin 38 the filter 10 can both be rotated about the longitudinal axis of the plug-in pin 38 and tilted such that the bottom side of the filter 10 does no longer extend parallel to the surface 37. This increases the freedom of movement of the patient.

As shown in FIG. 2 the depth of the insertion opening 43, configured as pocket hole, relative to the length of the plug-in pin 38 is selected such that the filter 10 is arranged at a distance to the surface 37. If the surface 37 is a patient's skin, this prevents the filter 10 from causing pressure sores on the patient's skin. Further the length of the plug-in pin 38 may be selected such that, depending on the filter 10 used and the diameter of the administering line 14, the administering line 14 rests on the surface 37. Since the filter 10 can be tilted owing to the configuration of the plug-in pin 38, the dimensional differences between the diameter of the administering line 14 and the length of the plug-in pin 38 may be compensated for. The ball-and-socket-type configuration of the connection between the filter 10 and the adhesive plaster 11 thus serves for compensating purposes if filters 10 and administering lines 14 are used which are not completely mating. If a syringe with a larger diameter is connected to the inlet stud 12 of the filter 10 for a short period, the filter 10 may be taken off the plug-in pin 38 of the adhesive plaster 11 and placed again onto the plug-in pin 38 when the liquid from the syringe has been administered. Painful removal of adhesive strips fixing the filter 10 is not necessary.

To allow the filter 10 to be directly fastened to the surface of a patient's skin 37 without using the adhesive plaster 11 a side 44 facing the adhesive plaster 11 comprises knops 45 such that air may freely circulate between the filter 10 and the surface of the skin 37. The hemispherical and singularly arranged knops 45 irritate the skin to a smaller extent than ribs or similar on the filter bottom side and prevent pressure sores or injuries caused by sharp edges.

To facilitate removal of the adhesive plaster 11 the adhesive plaster 11 comprises a flap 46 which is not coated with adhesive.

As can be seen from FIG. 3 the adhesive plaster 11 has a larger diameter than the filter 10. When the filter 10 is placed onto the plug-in pin 38 of the adhesive plaster 11, the plug-in pin 38 and the insertion opening 43 cannot be seen from above. Since the plug-in pin 38 and the insertion opening 43 are both arranged in the middle of the adhesive plaster 11 and the filter 12, respectively, the plaster is provided with a circle 47 whose diameter is slightly larger than that of the filter 10 so that the filter 10 can also be easily centered relatively to the adhesive plaster 11 from above. This considerably facilitates attachment of the filter 10 onto the plug-in pin 38 of the adhesive plaster 11.

FIGS. 4 and 5 show a second embodiment of an administering device. For example, a filter 50 is used over long periods for infusion of liquids and may be attached to the patient's body, clothes or bedclothes. In the embodiment shown the filter 50 is substantially triangular and flat. During the infusion process it must be ensured that no contaminants or gas bubbles are transported together with the infusion liquid to the patient's body. To guarantee that the filter 50 is not incorrectly connected, the filter 50 is of substantially triangluar shape with the vertex of the triangle pointing to the direction of flow. To make the direction of flow clearly identifiable, the filter may also be of funnel-shaped or similar configuration.

The liquid is fed via an administering line 51 into the left-hand filter half 52 of the filter 50 as shown in FIG. 5. The left-hand filter half 52 is separated from the right-hand filter half 53 by a hydrophilic membrane 54. It is a feature of the hydrophilic membrane 54 that up to a relatively high pressure, which is not reached during the infusion process, only liquids and no gases can penetrate the hydrophilic membrane 54. In the upper portion of the filter a hydrophobic membrane 55 is arranged which can only be penetrated by gases and not by liquids. The hydrophobic membrane covers two openings 61 through which gases leave the filter 50. Only liquid flowing through an outlet line 60 into a cannula leading to the patient's body can penetrate the hydrophilic membrane 54 and enter the right-hand filter half 53.

To fasten the filter 50 to the surface of a patient's skin or to a surface of an object the adhesive plaster 11 described in the first embodiment can be used. Since provision of a pocket hole in the filter portion is difficult when the filter is of flat configuration, the filter 50 comprises a stud 62 which is positively connected with the upper portion of the filter 50 on which the administering line 51 is retained. The flat stud 62 comprises a round insertion opening 63 whose inner diameter is larger than the diameter of the stem of the plug-in pin 38 and smaller than the head diameter of the plug-in pin 38. To fasten the filter 50 to the adhesive plaster 11 the filter 50 is placed onto the plug-in pin 38 such that the elastic elements 39 of the plug-in pin 38 are compressed by the insertion opening 63 and resume their original shape when they have penetrated the insertion opening 63. Thus the filter 50 is retained on the adhesive plaster 11 by means of a releasable snap connection. Like the filter 10 of the first embodiment the filter 50 can be detached by simply taking it off the plug-in pin 38.

To prevent the filter 50 from resting on the surface of the skin or the surface of an object to which the adhesive plaster 11 is fastened, the plug-in pin may comprise a bulge at the end facing the adhesive plaster 11, whose diameter is larger than the insertion opening 63. Further, the filter 50 may comprise another stud with an insertion opening so that the filter 50 is connectable at several places with a plug-in pin of an adhesive plaster.

Further, the stud 62 is provided with an oblong hole 64. A tape can be threaded through the oblong hole 64 so that the filter 50 can be fastened with the tape and a clamping device provided on the tape to the patient's clothes. By means of the tape threaded through the oblong hole 64 the filter can be fastened to an infusion stand, the clothes or any other object.

Although a preferred embodiment of the invention has been specifically illustrated and described herein, it is to be understood that minor variations may be made in the apparatus without departing from the spirit and scope of the invention, as defined the appended claims.

We claim:

1. A device for administering liquids to a patient's body, comprising an administering part (10, 50) through which liquid can flow, and an adhesive plaster (11) for fixing the administering part (10, 50), wherein the adhesive plaster (11) comprises a first coupling part (38) which releasably engages with a second coupling part (43, 63) provided on the administering part (10, 50), characterized in that one of the two coupling parts (38; 43, 63) is configured as a plug-in pin (38) and the other coupling part as a round insertion opening (43, 63) such that the administering part (10, 50) is rotatable relatively to the adhesive plaster (11) about an axis extending vertically to the plane of the adhesive plaster.

2. The device according to claim 1, characterized in that the two coupling parts (38; 43, 63) are configured as snap elements.

3. The device according to claim 2, characterized in that the plug-in pin (38) keeps the administering part (10, 50) at a distance to a surface (37) on which the adhesive plaster (11) is stuck.

4. The device according to claim 1, characterized in that the plug-in pin (38) keeps the administering part (10, 50) at a distance to a surface (37) on which the adhesive plaster (11) is stuck.

5. The device according to claim 1, characterized in that the plug-in pin (38) is provided on the adhesive plaster (11) and the insertion opening (43, 63) on the administering part (10, 50).

6. The device according to claim 1, characterized in that the adhesive plaster (11) comprises a non-adhesive flap (46).

7. The device according to claim 1, characterized in that the administering part (50) further comprises an oblong hole (64) for fastening the administering part (50) with a tape.

8. The device according to claim 1, characterized in that the surface (14) of the administering part (10) facing the adhesive plaster (11) is provided with knops (45).

9. The device according to claim 1, characterized in that the plug-in pin (38) comprises a spherical thickened head which allows the administering part (10, 50) to be tilted.

* * * * *

UNITED STATES PATENT AND TRADEMARK OFFICE
CERTIFICATE OF CORRECTION

PATENT NO. : 6,428,514 B1
DATED : August 6, 2002
INVENTOR(S) : Goebel et al.

It is certified that error appears in the above-identified patent and that said Letters Patent is hereby corrected as shown below:

<u>Title page,</u>
Item [22], should read as follows:

-- [22]  PCT Filed:          Oct. 9, 1998 --

Insert:  -- [86]  PCT No.:          PCT/EP98/06427

§371 (c)(1),
(2), (4) Date:          Jul. 5, 2000

[87]  PCT Pub. No.:     WO99/25414
      PCT Pub. Date:    May 27, 1999 --

Signed and Sealed this

Fifteenth Day of April, 2003

JAMES E. ROGAN
*Director of the United States Patent and Trademark Office*